US006936414B2

(12) United States Patent
Gundling

(10) Patent No.: US 6,936,414 B2
(45) Date of Patent: *Aug. 30, 2005

(54) NUCLEIC ACID ISOLATION METHOD AND KIT

(75) Inventor: Gerard Gundling, Lake Forest, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/470,944

(22) Filed: Dec. 22, 1999

(65) Prior Publication Data

US 2002/0068821 A1 Jun. 6, 2002

(51) Int. Cl.$^7$ .......................... C12Q 1/68; C12P 19/34; C07H 21/00; A23J 1/00
(52) U.S. Cl. .......................... 435/6; 435/91.2; 530/412; 530/413; 530/419; 536/25.4; 536/25.41; 536/25.42
(58) Field of Search .................... 435/6, 91.2; 530/412, 530/413, 419; 536/25.4, 25.41, 25.42

(56) References Cited

U.S. PATENT DOCUMENTS

| | | | |
|---|---|---|---|
| 5,010,183 A | | 4/1991 | Macfarlane |
| 5,128,247 A | * | 7/1992 | Koller .......................... 435/91 |
| 5,234,809 A | | 8/1993 | Boom et al. |
| 5,300,635 A | | 4/1994 | Macfarlane |
| 5,405,951 A | | 4/1995 | Woodard |
| 5,482,834 A | | 1/1996 | Gillespie |
| 5,523,231 A | | 6/1996 | Reeve |
| 5,750,338 A | * | 5/1998 | Collins et al. .................. 435/6 |
| 5,945,515 A | * | 8/1999 | Chomczynski .............. 530/412 |
| 5,958,677 A | | 9/1999 | Lee et al. |
| 5,973,137 A | | 10/1999 | Heath |
| 5,973,138 A | | 10/1999 | Collis |

FOREIGN PATENT DOCUMENTS

| | | |
|---|---|---|
| EP | 0391608 | 10/1990 |
| EP | 0757106 A2 * | 5/1997 |
| EP | 0 818 461 A | 1/1998 |
| GB | 2221466 | 2/1990 |
| WO | 91 12079 A | 8/1991 |
| WO | WO 92/18514 * | 10/1992 |
| WO | 95 33827 A | 12/1995 |
| WO | 96 09379 A | 3/1996 |
| WO | 96 18731 A | 6/1996 |
| WO | 98 31840 A | 7/1998 |

OTHER PUBLICATIONS

Boom, R., et al., "Rapid and Simple Method for Purification of Nucleic Acids", *Journ or Clin Microbiology*, 38(3):495–503 (1990).

Davies, M. J., et al., "Isolation of Plasmid DNA Using Magnetite as a Solid–Phase Adsorbent", *Analytical Biochemistry*, 262:92–94 (1998).

* cited by examiner

*Primary Examiner*—Jezia Riley
(74) *Attorney, Agent, or Firm*—Wood, Phillips, Katz, Clark & Mortimer

(57) ABSTRACT

Provided herein is a method for separating nucleic acid from a test sample comprising the steps of contacting a test sample with a metal oxide support material and a binding buffer to form nucleic acid/metal oxide support material complexes, separating the complexes from the test sample; and eluting the nucleic acid from the metal oxide support material.

15 Claims, 2 Drawing Sheets

NUCLEIC ACID ISOLATION METHOD AND KIT

FIELD OF THE INVENTION

The present invention relates to methods and kits for isolating nucleic acid and more particularly relates to methods and kits for isolating nucleic acids that do not use significant concentrations of flammable components.

BACKGROUND OF THE INVENTION

Several methods for isolating nucleic acid from various sources are well known. Early methods employed organic solvents, such as phenol and/or chloroform, to selectively precipitate and then remove proteins from a nucleic acid containing solution. Once the protein was removed, dissolved nucleic acid then could be precipitated using alcohol and collected on a solid surface. An appropriate buffer then was used to solubilize the nucleic acid and thereby remove it from the solid surface.

As previously mentioned, early methods for purifying nucleic acid sequences typically employed organic solvents to differentially precipitate nucleic acid sequences from proteins and other undesired matter found in a source material. Once precipitated, the nucleic acid is easily collected on solid a substrate such as a glass stir rod before it is solubilized in a purified state. The affinity nucleic acid displays for solid substrates in the presence of a chaotropic agent has also been exploited to purify nucleic acid. These sample prep methods in addition to employing chaotropic agents typically use organic solvents, such as an alcohol, to assure that the nucleic acid binds the solid substrate or stays bound to the substrate during washing procedures. While such procedures use relatively low concentrations of organic solvents, in comparison to early methods of isolating nucleic acid where organic solvents were the only reagents employed, the alcohol concentrations used in these procedures nevertheless give rise to significant disposal and safety concerns especially when high volumes of samples are processed.

With the advent of nucleic acid amplification reactions such as, for example, the polymerase chain reaction (PCR), the ligase chain reaction (LCR), and other similar procedures designed to synthesize multiple copies of a target nucleic acid sequence, isolating nucleic acid sequences from source materials (variously referred to as "sample preparation" or "sample prep") has become an increasingly important research area. Several considerations, outside of the mere purification of nucleic acid sequences, make discovery of useful sample prep methods challenging. For example, sample-to-sample contamination with extraneous nucleic acid is a well documented and significant concern. Additionally, initial samples that contain the desired nucleic acid sequence (or "target nucleic acid sequence"), often times contain very small concentrations of the target sequence, as well as comparatively large concentrations of extraneous nucleic acid. Moreover, sample prep often times is performed in areas that are highly regulated in terms of the reagents that can be used and ultimately discarded. Further, in instances where the nucleic acid is being purified for purposes of use in an amplification reaction, it is important for the nucleic acid to ultimately reside in a buffer that does not comprise components that inhibit enzymes commonly employed in amplification reactions. Hence, several considerations, beyond the mere purification of nucleic acid sequences, must be accounted for in the design of a useful sample prep method.

Thus, there is a need for a sample prep method that provides for quantitative isolation of nucleic acid with minimal handling and does not need flammable organic solvents.

SUMMARY OF THE INVENTION

The present invention provides a method for separating nucleic acid from a test sample comprising the steps of contacting a test sample with a metal oxide support material and a binding buffer to form nucleic acid/metal oxide support material complexes, separating the complexes from the test sample; and eluting the nucleic acid from the metal oxide support material. The binding buffer generally will comprise a chaotropic agent and a detergent, but may also comprise organic solvents and reducing agents. Preferably the binding buffer will have a flash point of greater than 125 degrees Fahrenheit. The method is sufficiently robust that it can purify nucleic acid from distinct nucleic acid containing sources such as bacteria and virus such that it later can be detected.

DETAILED DESCRIPTION OF THE INVENTION

Figure 1A:
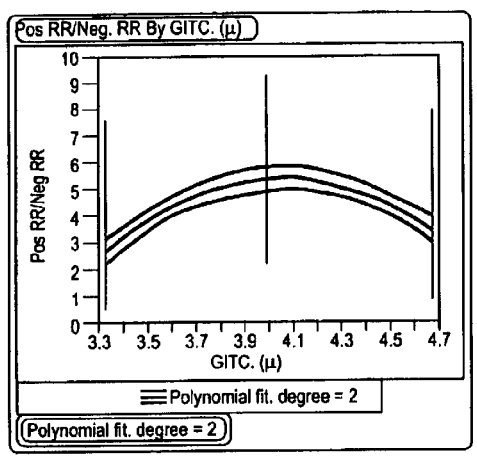
FIGS. 1A–1F and FIGS. 2A–2F represent computer analysis of data obtained in the Examples.

The methods provided herein employ a metal oxide support material to separate nucleic acid from other, but not necessarily all, components found in a test sample. Specifically, the metal oxide is employed to purify nucleic acid from other components in a test sample. It has been discovered that using metal oxide support materials as taught herein provides several important advantages over currently available sample preparation methods. For example, metal oxides have a high affinity for nucleic acid sequences and therefore sample-to-sample contamination is minimized because nucleic acid can controllably be bound to the metal oxide support without escaping to undesired areas. Additionally, metal oxide supports provide for a more quantitative purification of nucleic acid in a test sample and therefore even small amounts of a desired nucleic acid that may be present in the test sample are collected. Moreover, metal oxide particles can be employed to separate nucleic acid from a test sample with low organic-solvent concentrations (or, significantly, without the use of organic solvents) such as alcohol, phenol or chloroform, which are commonly employed according to other sample prep methods, but pose significant disposal concerns. Further, nucleic acid can be eluted from metal oxide supports using buffers that are completely compatible with amplification reactions. In other words, nucleic acid separated from a test sample in the manner provided herein directly can be employed in an amplification reaction without the need to exchange the elution buffer with a buffer compatible with an amplification reaction.

Additionally, the method provided herein can be employed to separate both DNA and the various forms of RNA from a single test sample. Hence, the method provided herein can be employed to separate nucleic acid from various different cells and/or organisms in the same test sample such that it later can be detected.

Generally, the method comprises contacting a test sample with a metal oxide support material and a binding buffer. In the presence of binding buffer, nucleic acid of all types, such as DNA and the various forms of RNA, contained in the test sample binds the metal oxide support material. The metal oxide support material and any nucleic acid bound thereto then can be separated from the test sample. If desired, the support material, and any bound nucleic acid, can be washed before the nucleic acid is eluted using an elution buffer. Any eluted nucleic acid can then be detected using any of a variety of well known detection techniques.

The term "test sample" as used herein means anything suspected of containing a nucleic acid. The test sample is, or can be derived from, any source such as, for example, biological sources including blood, ocular lens fluid, cerebral spinal fluid, milk, ascites fluid, synovial fluid, peritoneal fluid, amniotic fluid, tissue, fermentation broths, cell cultures, products of an amplification reaction, nucleic acid synthesis products and the like. Test samples can also be from, for example, environmental or forensic sources including sewage or cloth. The test sample can be used directly as obtained from the source or following a pretreatment to modify the character of the sample. Thus, the test sample can be pre-treated prior to use by, for example, preparing plasma from blood, isolating cells from biological fluids, homogenizing tissue, disrupting cells or viral particles, preparing liquids from solid materials, diluting viscous fluids, filtering liquids, distilling liquids, concentrating liquids, inactivating interfering components, adding reagents, purifying nucleic acids, and the like.

"Metal oxide support materials" as used herein means oxides and hydroxides of metallic elements in any of their various valence states. Thus, for example, oxides of aluminum, magnesium, titanium, zirconium, iron, silicon, nickel, chromium, zinc and combinations of the forgoing are metal oxide support materials. Iron oxides are preferred metal oxide support materials. Ferrous oxide ($Fe_3O_4$) and ferric oxide ($Fe_2O_3$) are therefore preferable metal oxide support materials. Metal oxide support materials can be in any configuration such as, for example, plates, particles, coatings, fibers, porous structures such as filters. Due to their high surface area, particles are the preferred configuration of the metal oxide support material.

"Binding buffers" facilitate binding of nucleic acid present in a test sample to metal oxide support materials. It has been found that nucleic acid will bind to metal oxide support materials in an extensive variety of buffers without regard to the pH of the buffer. Hence, the binding buffer can have an acidic pH (less than 7), neutral pH (equal to 7), or a basic pH (greater than 7). Binding buffers will generally comprise a buffering system. Buffering systems are well known and a matter of choice for those skilled in the art. Buffering systems are typically an aqueous solution of a weak acid and its corresponding base, such as, for example, sodium phosphate and phosphoric acid. Preferably, binding buffers have a pH of between 3 and 12, more preferably between 3 and 11, and most preferably between 4 and 10. The binding buffers may also contain detergents well known to those skilled in the art such as non-ionic detergents, ionic detergents, zwitterionic detergents, at a total concentration of between 1% and 25% and preferably between 5% and 20%.

In cases where nucleic acid is purified directly from, for example cells or virus particles which contain nucleic acid, the binding buffer preferably further comprises a chaotropic agent at a concentration of between 2M and 10M, preferably between 3M and 6M. Chaotropic agents are well known in the art and include entities that break down, or solubilize, proteins. Exemplary chaotropic reagents include, but are not limited to guanidine isothiocyanate (GITC), guanidine HCl, potassium iodide, urea and the like. Reducing agents such as mercaptoethanol, dithiothreotol, and 2-mercaptoethanesulfonic acid can also be added to the binding buffer at concentrations between 25 mM and 150 mM, and preferably 50 mM to 100 mM.

Although it is not necessary, the binding buffer may also include an alcohol, or other organic solvent, at concentrations that do not result in a binding buffer having a flash point greater than 125° Fahrenheit. The flashpoint of the buffer can be determined using any of the well known methods for determining the flash point of a liquid. Generally, organic solvents employed at concentrations of less than 15% will result in a binding buffer having a flash point of greater than 125° Fahrenheit. Lower alcohols such as methanol, ethanol, propanol and isopropanol are preferred alcohols in cases where a solvent is added to the binding buffer.

As mentioned previously, in the presence of the binding buffer, nucleic acid in the test sample will bind the support material. Upon formation of the complexes between the nucleic acid and support material, the support material can be separated from the binding buffer and remaining test sample. Depending upon the configuration of the support material, the method of separation will be a matter of choice for one skilled in the art. For example, if the support material is in a particulate form, the support material can be, for example, sedimented and the remaining liquid material can be removed from the support through aspiration or simply pouring the liquid off of the support material. Given the composition of the support materials according to the present invention, it is preferable to use a magnetic field to facilitate sedimentation or isolation of particulate support materials.

Nucleic acid sequences complexed to the support material, if desired, can be washed with any buffer that does not dissociate the nucleic acid from the support material. Wash buffers typically are employed to cleanse the support material, and any nucleic acid complexed thereto, of any residual and undesired test sample components. Such wash buffers are well known in the art and typically contain solutions of detergents such as those previously mentioned in similar concentrations. Such detergents are typically diluted in buffering systems, also defined above.

Whether or not washed, nucleic acid complexed to the support material may be removed or dissociated from the metal oxide support material using water or an elution buffer. An "elution buffer" according to the present invention can be any reagent or set of reagents that separates bound nucleic acid from the metal oxide support material. Preferably, such a reagent will be compatible with detection system employed for the nucleic acid, and particularly compatible with reagents employed in nucleic acid amplification systems. Water, that may be distilled, deionized, or otherwise purified, may serve as an elution buffer for purposes of the present invention. Elution buffers (typically comprising a buffering system as described above) containing phosphate, or bicine also have been found to be suitable elution buffers and others can easily be found empirically using ordinary skill in the art such as by contacting metal oxide-nucleic acid complexes with a buffer and determining if separation has occurred (as exemplified below). The elution buffer may contain inorganic or organic phosphate through addition of sodium phosphate or organophosphate compounds which are organic compounds containing at least one phosphate functionality at concentrations of between 10 mM to 300 mM, preferably between 10 mM and 100 mM. O-phosphoserine, phosphoethanolamine, carbamyl phosphate, phosphocreatine, adenosine monophosphate (AMP), and phosphotungstic acid are examples of organophosphate compounds. Suitable pH's for elution buffers can be between 6 and 10, and preferably between 7 and 9.

Purified nucleic acid then can be detected using assays well known in the art. For example, sandwich hybridization assays can be employed with or without an amplification step prior to detection. Well known amplification reactions such as, for example, TMA, QB-replicase, NASBA, SDA, LCR, and PCR are examples of amplification reactions that can be employed to amplify nucleic acid purified according to the present invention.

The above amplification reactions typically employ names amplification reagents. The phrase "amplification reaction reagents" as used herein means reagents which are well known for their use in nucleic acid amplification reactions and may include but are not limited to: primers, probes, a single or multiple reagent, reagents, enzyme or enzymes separately or individually having reverse transcriptase, polymerase, and/or ligase activity; enzyme cofactors such as magnesium or manganese; salts; nicotinamide adenine dinucleotide (NAD); and deoxynucleoside triphosphates (dNTPs) such as, for example, deoxyadenosine triphosphate, deoxyguanosine triphosphate, deoxycytodine triphosphate and thymidine triphosphate. The exact amplification reagents employed are largely a matter of choice for one skilled in the art based upon the particular amplification reaction employed.

It was discovered that amplification of nucleic acid, as purified above, can be performed in the elution buffer employed to dissociate the nucleic acid from the metal oxide support material. In particular, amplification reagents can be combined with the nucleic acid in the elution buffer and amplification of the nucleic acid can directly be performed.

The present invention further provides kits comprising suitably packaged reagents for isolating nucleic acid according to the present invention. The kits may include a metal oxide support material, a binding buffer (as described above), and an elution buffer (as described above). The kit may also contain other suitably packaged reagents and materials for using the isolated nucleic acid in a particular assay. By way of example, the kit may further include, nucleic acid amplification primers and/or nucleic acid probes, buffers, nucleotides, enzymes, conjugates, and the like.

The Examples that follow illustrate preferred embodiments of the present invention and are not limiting of the claims and specification in any way.

EXAMPLES

Example 1

Binding and Elution of Radio-Labeled RNA Using Metal Oxide Support Materials

In this example, radio-labeled RNA was bound to various metal oxide support materials, washed, and then eluted from the support materials. The counts per minute (CPM) were monitored throughout the course of the process to determine the amount of bound RNA as well as the amount of RNA lost during the wash, and finally, the amount of the RNA eluted.

The radio-labeled RNA employed in this experiment was generated using the Riboprobe T7 RNA polymerase transcription system and pGEMEX-1 positive control template from Promega Corporation. In the binding and elution experiment, approximately 8,000,000 CPM of the radio-labeled probe was added to suspensions of 5 mg $Fe_3O_4$ or $Fe_2O_3$ metal oxide particles (obtained from ISK Magnetics; Valparaiso, Ind.) in 6 ml of a guanidine isothiocyanate-detergent solution (6M GITC, 10% Tween-20, 16 mM cetyltrimethylammonium bromide, 100 mM sodium acetate, 100 mM Dithiothreitol, pH 4.2, 7.5% ethanol). After adding the RNA to the respective particle suspensions, the suspensions were briefly vortexed and incubated at 37° C. for 30 minutes.

After the incubation, the metal oxide particles were pulled to the sides of the respective microfuge tubes with a magnet and the supernatants were aspirated with a pipette. The CPM of the supernatants were determined and are recorded in Table 1, below, as "Unbound" RNA.

The particles were then washed by adding 0.5 ml of a wash solution and vortexing the newly formed suspension before pulling the particles to the side of the microfuge tube as above and aspirating the wash solution from the microfuge tube. The particles were washed twice with a guanidinium isothiocyanate-detergent solution (2M GITC, 5% Tween-20, 50 mM KOAc, pH 6) and twice with 50 mM Tris buffer, pH 8.0. The washes were pooled and the amount of label removed from the particles was determined and is recorded in Table 1 as "Wash".

After the wash solution was aspirated, 200 microliters of elution buffer was added to the tubes containing the washed particles. The elution buffer was a solution of 100 mM o-phosphoserine (Sigma Chemical Co., St. Louis, Mo.) and 300 mM Tris base with a final pH of 8.0. After addition of the elution buffer, the newly formed particle suspensions were briefly vortexed and the suspension was incubated at 70° C. for 30 minutes. After incubation the particles were captured on the sides of the tubes using a magnetic rack and the eluant removed. The CPM were determined and is recorded in Table 1 as "Eluant 1". Fresh elution buffer was added to the particles and the elution process was repeated and the CPM of the second elution is recorded in Table 1 as "Eluant 2".

The particles were resuspended in a third 200 microliter aliquot of elution buffer and a sample containing elution buffer and resuspended particles was used to determine the amount of probe which was not released from the particles. This is recorded in Table 1 as "Bound".

All values shown in Table 1 are recorded as a percent of the total CPM.

TABLE 1

| | % Total CPM | | | | |
|---|---|---|---|---|---|
| Particles | Unbound | Wash | Eluant 1 | Eluant 2 | Bound |
| $Fe_3O_4$ | 10 | 2 | 70 | 15 | 3 |
| $Fe_2O_3$ | 7 | 2 | 63 | 10 | 18 |

As shown by the data in Table 1, the ferric oxide and ferrous oxide particles bound RNA and the RNA was eluted from the respective particles with the phosphate buffer.

Example 2

Elution of RNA from $Fe_3O_4$ Using Various Phosphate Concentrations

In this example, radio-labeled RNA prepared as in Example 1 was bound to $Fe_2O_3$ magnetic particles, washed, and eluted with various concentrations of sodium phosphate ($Na_2HPO_4$) buffer. The elution buffer concentrations ranged from 10 to 50 mM $Na_2HPO_4$ (pH 9). Approximately 23,000, 000 CPM of the radio-labeled nucleic acid was added to a suspension of 25 mg $Fe_2O_3$ metal oxide particles (0.25 ml of a 10% w/vol suspension of particles in water) in 30 ml of a guanidine isothiocyanate-detergent solution (4M GITC, 10% Tween-20,16 mM cetyltrimethylammonium bromide, 100 mM 2-mercaptoethanesulfonic acid, 100 mM potassium acetate, pH 6). 5 ml of water was then added to the suspension to simulate the dilution effect of five 1 ml samples. The suspension was briefly vortexed and was divided into 5 equal aliquots of 7 ml each and all of the suspensions were incubated at 37° C. for 20 minutes.

After the incubation, the metal oxide particles were pulled to the sides of the respective microfuge tubes with a magnet and the supernatants were aspirated with a pipette. The amount of unbound probe was monitored with a Geiger counter and very low amounts of radio-labeled nucleic acid were not captured when compared to the amount of radioactivity bound to the particles monitored in an identical fashion. The exact CPM of the unbound material was not determined.

The particles were then washed by adding 0.5 ml of a wash solution and vortexing the newly formed suspension before pulling the particles to the side of the microfuge tube as above and aspirating the wash solution from the microfuge tube. The particles were washed twice with (2M GITC, 5% Tween-20, 50 mM KOAc, pH 6) and twice with (50 mM Tris buffer, pH 8.0). The washes were monitored with a Geiger counter and the amount of radioactivity released during the wash procedure was also found to be negligible. The samples were eluted with 0.2 ml of each of the elution buffers at 73° C. for 10 minutes. The eluant was collected after magnetic capture of the particles and saved. The elution protocol was repeated and the second eluant was also saved. A third aliquot of elution buffer was also added to the particles and the particles in suspension were used to determine the amount of bound probe. 20 µl aliquots of each of the eluants and paritcle suspensions were mixed with 5 ml of scintillation fluor and counted. Table 2 reports the concentrations of sodium phosphate in the elution buffers employed in this experiment (column 1), the percentage of the total counts recovered after a first and second elution (columns 2 and 3), and the percentage of the counts remaining on the magnetic particles after both elutions ("Bound").

TABLE 2

| Elution Buffer | Elution 1 | Elution 2 | Bound |
| --- | --- | --- | --- |
| 10 mM $Na_2HPO_4$ | 45 | 20 | 35 |
| 20 mM $Na_2HPO_4$ | 68 | 18 | 14 |
| 30 mM $Na_2HPO_4$ | 75 | 16 | 9 |
| 40 mM $Na_2HPO_4$ | 76 | 16 | 8 |
| 50 mM $Na_2HPO_4$ | 79 | 14 | 7 |

As shown by Table 2, various concentrations of phosphate buffer eluted the RNA from the metal oxide particles.

Example 3

Use of Organophosphate Elution Buffers

In this example, various organophosphate buffers were tested for their ability to elute nucleic acid from a metal oxide support material compared to inorganic phosphate buffers. All of the organophosphate compounds employed in the elution buffers were obtained from Sigma Chemical Co. Except where indicated in Table 3, all buffers were made at 50 mM and pHed with 1 M tris base to a final pH of between 6.5 and 9. As in the previous examples, the radio-labeled RNA was made as in Example 1. Approximately 1,000,000 CPM of the radio-labeled RNA was added to a suspension of 10 mg $Fe_2O_3$ metal oxide particles in 12 ml of a guanidine isothiocyanate-detergent solution (6M GITC, 10% Tween-20,16 mM cetyltrimethylammonium bromide, 100 mM sodium acetate, 100 mM Dithiothreitol, pH 4.2, 7.5% ethanol). 2 ml of water was added to the suspension to simulate the addition of sample. The suspension was briefly vortexed and incubated at 37° C. for 25 minutes. The particles were collected magnetically and the supernatant removed. No significant loss of signal was observed in the supernatant when checked by Geiger counter. The particles were washed by resuspending the particles in 6 ml of 50 mM potassium acetate, pH 6.0. The particles were collected magnetically and the wash fluid was removed. No significant loss of signal was observed in the supernatant when checked by Geiger counter. The wash procedure was repeated. The particles were then resuspended in 6 ml of the potassium acetate wash fluid, mixed well, and 0.5 ml aliquots were dispensed into 10 separate 1. 5 ml microfuge tubes. The tubes were transferred to a magnetic rack, the particles collected on the sides of the tubes, and the wash fluid was removed. 100 microliters of various elution buffers were then added to the microparticles and incubated at 70° C. for 10 minutes. 50 micoliters of the eluted samples was then counted in a scintillation counter to determine the amount of released probe. The approximate total counts of starting material (nucleic acid) was 40,000 CPM/sample. Table 3 gives the results of this experiment and reports the elution buffer and the counts released with that elution buffer.

TABLE 3

| Elution Buffer | Released Counts |
| --- | --- |
| Adenosine monophosphate (pH 6.5) | 17,229 |
| Phosphocreatine (pH 7) | 9172 |
| O-phosphoryethanolamine (pH 7) | 3379 |
| Carbamyl phosphate (pH 7) | 27,717 |
| Phosphonoacetic acid (pH 8) | 29,367 |
| Phosphorylcholine (pH 7) | 404 |
| Phosphotungstic acid (pH 8) | 34,825 |
| O-phospho-di-serine (pH 7) | 18,807 |
| 30 mM $Na_2HPO_4$ (pH 8) | 29,277 |
| 30 mM $Na_2HPO_4$ (pH 9) | 20,468 |

As shown by Table 3, organophosphate buffers are suitable buffers for eluting bound nucleic acid from metal oxide support materials.

Example 4

Extraction of RNA from HIV Virions in Plasma

In this example, HIV nucleic acid was extracted from four test panels of plasma that contained various levels of the HIV virions using the metal oxide particles described above. Negative plasma was used as a negative control. Nucleic acid from the plasma samples was also extracted using the commercially available Qiagen viral nucleic acid extraction kit (Qiagen Inc.; Valencia Calif.). The HIV nucleic acid in the samples was analysed using the Abbott LCx® Quantitiative HIV assay (available from Abbott Laboratories; Abbott Park, Ill.).

The respective sample preparation procedures were performed on 1 ml of plasma samples from each of the four test panels and the negative control. The Qiagen procedure was performed on the panels in accordance with the manufacturer's instructions and the samples quantitated using the Abbott LCx® HIV assay. Test panels 1–4 contained 28 virions/ml, 110 virions/ml, 800 virions/ml and 10,000 virions/ml respectively. The metal oxide procedure was performed by mixing 1 ml of test plasma sample with 6 ml of binding buffer (5M guanidinium isothiocyanate, 10% Tween-20, 16 mM cetyltrimethylammonium bromide, 100 mM dithiothreitol, 100 mM Na acetate, pH 4.1) and 5 mg of $Fe_2O_3$ particles. The lysate was incubated at 37° C. for 20 minutes. The particles were then washed by adding 0.5 ml of a wash solution and vortexing the newly formed suspension before pulling the particles to the side of the microfuge tube as above and aspirating the wash solution from the microfuge tube. The particles were washed twice with 2M GITC, 5% Tween-20, 50 mM KOAc, pH 6, and twice with 50 mM Tris buffer, pH 8.0. After the wash solution was aspirated, 200 microliters of elution buffer was added to the tubes containing the washed particles. The elution buffer was a solution of 50 mM o-phosphoserine and 150 mM Tris base with a final pH of 8.0. After addition of the elution buffer, the newly formed particle suspensions were briefly vortexed and the suspension was incubated at 70° C. for 30 minutes. After incubation the particles were captured on the sides of the tubes using a magnetic rack and the eluant removed. 50 µl of the solutions recovered according to the respective sample prep procedures were then subject to amplification and detection.

50 µl aliquots from the respective sample prep methods were reverse transcribed and amplified using PCR. RT-PCR was performed using 1X EZ Buffer, 2.5 mM manganese chloride, dNTPs (dATP, dGTP, dTTP and dCTP) present at a final concentration of 0.15 mM each, and recombinant *Thermus thermophilus* polymerase at a concentration of 5 units/reaction. The labeled primer was used at a concentration of 40 nM and the unlabeled primer concentration was used at a concentration of 40 nM. The probe, which was labeled as specified above and that ultimately hybridizes with the product of the labeled primer prior to detection of the resultant hybrid complex, was used at a concentration of 10 nM.

Reaction mixtures were reverse transcribed and amplified in a Perkin-Elmer 480 Thermal Cycler. Reaction mixtures were first incubated at 62° C. for 30 minutes to reverse transcribe the RNA, followed by 2 minutes at 94° C. PCR amplification was then initiated through a touchdown or step-down protocol to aid in the stringency of the reaction in the early stages of amplification. This utilized 8 cycles as follows: 1 cycle at 94° C. for 30 seconds then 70° C. for 80 seconds followed by 1 cycle of 94° C. for 30 seconds then 69° C. for 80 seconds, followed by 1 cycle of 94° C. for 30 seconds then 68° C. for 80 seconds, followed by 1 cycle of 94° C. for 30 seconds then 67° C. for 80 seconds, followed by 1 cycle of 94° C. for 30 seconds then 66° C. for 80 seconds, followed by 1 cycle of 94° C. for 30 seconds then 65° C. for 80 seconds, followed by 1 cycle of 94° C. for 30 seconds then 64° C. for 80 seconds, followed by 1 cycle of 94° C. for 30 seconds then 63° C. for 80 seconds. Further amplification was then accomplished with 35 cycles at 94° C. for 30 seconds then 62° C. for 80 seconds. After the reaction mixtures were thermal cycled, all duplicates were pooled and mixed by pipetting to eliminate any variation due to cycling. The mixtures were then split and denatured for 5 minutes at 97° C. Following this, probe oligo hybridization was accomplished by lowering the temperature to 15° C. for 5 minutes The temperature was then lowered to 4° C. and samples were held at 4° C. until the reaction products were detected.

The results obtained for the four test panels and negative control are shown in Table 4 below as copies/ml.

TABLE 4

| Sample Prep Method | Negative Control | Panel 1 | Panel 2 | Panel 3 | Panel 4 |
|---|---|---|---|---|---|
| Qiagen | 5 | 75 | 90 | 900 | 9000 |
| Metal Oxide | 9 | 80 | 100 | 850 | 10,000 |

As shown in the results from Table 4 the metal oxide sample prep procedure successfully extracted nucleic acid from plasma in amounts sufficient for amplification and detection.

Example 5

Extraction of Nucleic Acids from HIV and HBV Virions in Plasma

In this example, HIV nucleic acid (RNA) and HBV nucleic acid (DNA) was extracted from one ml of plasma that contained both HIV and HBV virions each at a concentration of 1000 virions/ml using the metal oxide particles described above. Negative plasma was used as a negative control. The lysis conditions were varied to cover a range of concentrations of GITC (3.33 to 4.66M), DTT (0 to 100 mM), Tween-20 (13.3 to 24%), and CTAB (0 to 24 mM) as well as pH (4 to 10), and temperature (35° C. to 55° C.). 45 different combinations of reagents and conditions were used in the lysis step with all samples being extracted with 3 ml of lysis buffer. 5 mg of Fe2O3 particles were used in each extraction. Each condition was used at least three times with the centerpoint conditions being used 30 times. The particles were washed twice with 2M GITC, 5% Tween-20, 50 mM KOAc, pH 6 and twice with 50 mM Tris buffer, pH 8.0. After the wash solution was aspirated, 200 microliters of elution buffer was added to the tubes containing the washed particles. The elution buffer was a solution of 50 mM o-phosphoserine and 150 mM Tris base with a final pH of 8.0. After addition of the elution buffer, the newly formed particle suspensions were briefly vortexed and the suspension was incubated at 70° C. for 30 minutes. After incubation the particles were captured on the sides of the tubes using a magnetic rack and the eluant removed. 50 µl of the solutions recovered according to the respective sample prep procedures were then subject to amplification and detection. The eluted material was split and analyzed using two PCR based assays, one for HIV and one for HBV. The assays are "beacon" assays and utilize a hybridization probe which has an increase in fluorescence upon the binding of the probe to amplified target material.

For the HIV assays, 50 µl aliquots from the respective sample prep methods were reverse transcribed and amplified using PCR. RT-PCR was performed using 1X EZ Buffer, 3 mM manganese chloride, dNTPs (dATP, dGTP, dTTP and dCTP) present at a final concentration of 0.100 mM each, and recombinant *Thermus thermophilus* polymerase at a concentration of 14.4 units/reaction. The forward primer (SEQ ID NO 1) was used at a concentration of 188 nM and the reverse primer (SEQ ID NO 2) was used at a concentration of 469 nM. The HIV beacon probe (SEQ ID NO 3) was used at a concentration of 100 nM. Reaction mixtures were reverse transcribed and amplified in a Perkin-Elmer 9700 Thermal Cycler using 96 well amplification trays. Reaction mixtures were first incubated at 59° C. for 30 minutes to reverse transcribe the RNA. PCR amplification was then accomplished with 5 cycles at 92° C. for 15 seconds then 59° C. for 30 seconds and then 72° C. for 15 seconds. This was followed by 55 cycles at 92° C. for 4 seconds then 64° C. for 8 seconds and then 72° C. for 4 seconds. The reactions were then heated to 92° C. for 30 seconds and then held at 45° C. for 15 minutes and then lowered to 25° C. The amount of signal was determined by reading the plate in a Cytofluor Series 4000 plate reader.

For the HBV assays, 50 μl aliquots from the respective sample prep methods were amplified using PCR. PCR was performed using 1X PCR Buffer, 3.5 mM magnesium chloride, dNTPs (dATP, dGTP, dTTP and dCTP) present at a final concentration of 0.100 mM each, and AmpliTaq Gold at a concentration of 7 units/reaction. The forward primer (SEQ ID NO 4) was used at a concentration of 200 nM and the reverse primer (SEQ ID NO 5) was used at a concentration of 300 nM. The HBV beacon probe (SEQ ID NO 6) was used at a concentration of 50 nM. Reaction mixtures were amplified in a Perkin-Elmer 9700 Thermal Cycler using 96 well amplification trays. Reaction mixtures were first incubated at 94° C. for 10 minutes to activate the enzyme. PCR amplification was then accomplished with 45 cycles at 94° C. for 60 seconds then 58° C. for 30 seconds. The reactions were then kept at 58° C. for 10 minutes, the temperature raised to 94° C. for 5 minutes and then held at 55° C. for 15 minutes and then lowered to 25° C. The amount of signal was determined by reading the plate in a Cytofluor Series 4000 plate reader.

Figure 1B:
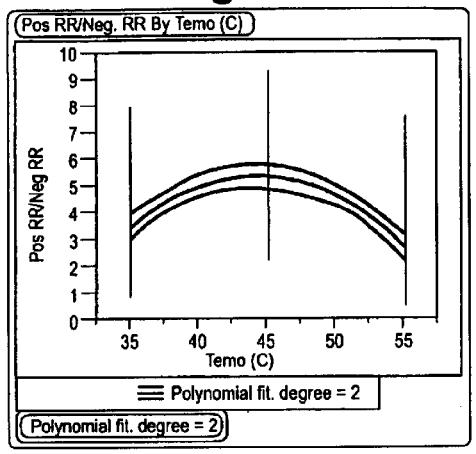
Figure 1C:
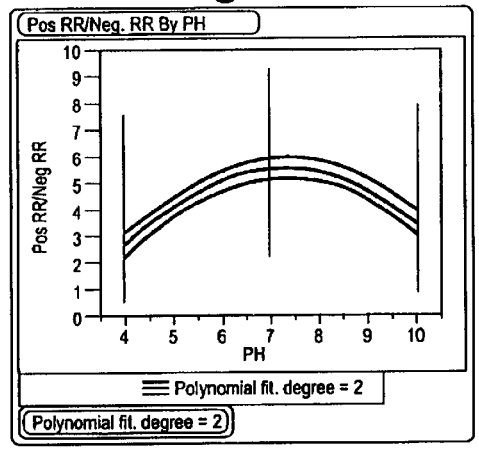
Figure 1D:
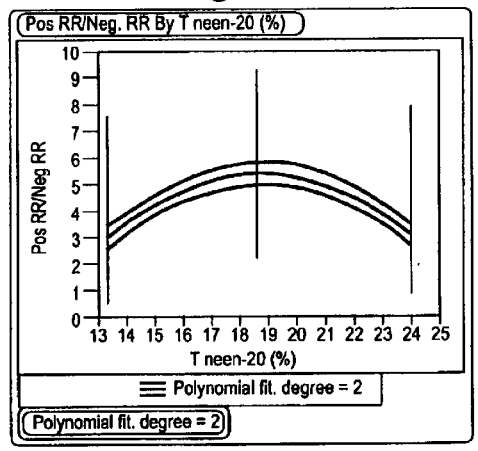
Figure 1E:
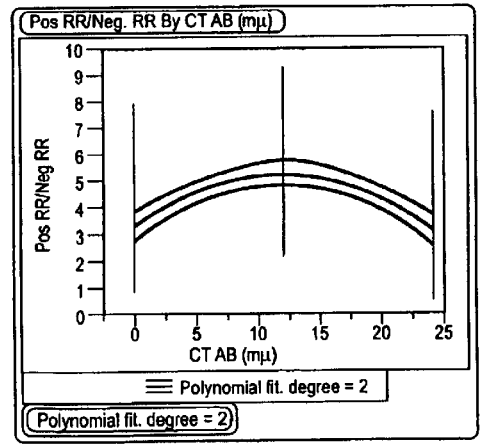
Figure 1F:
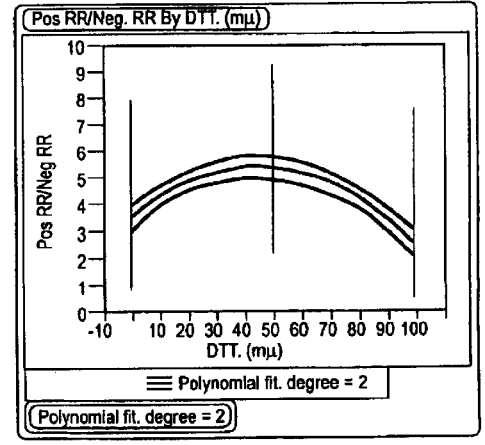
Figure 2A:
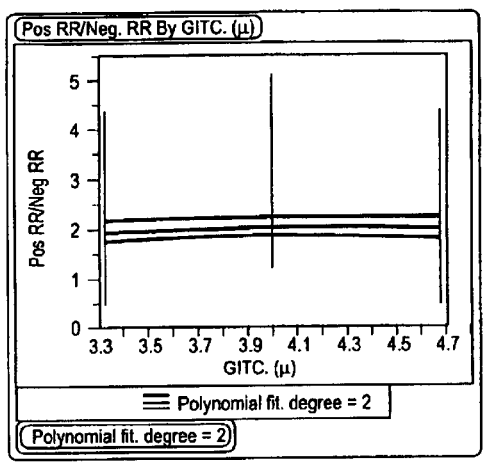
Figure 2B:
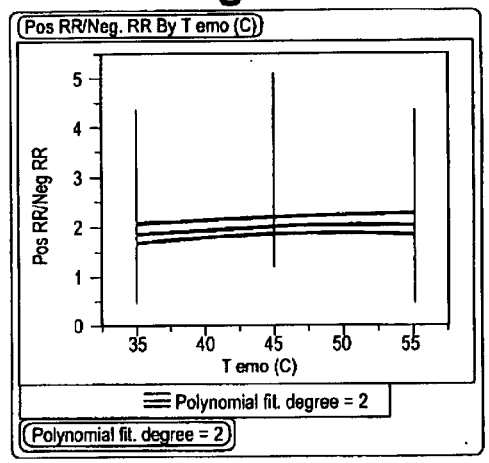
Figure 2C:
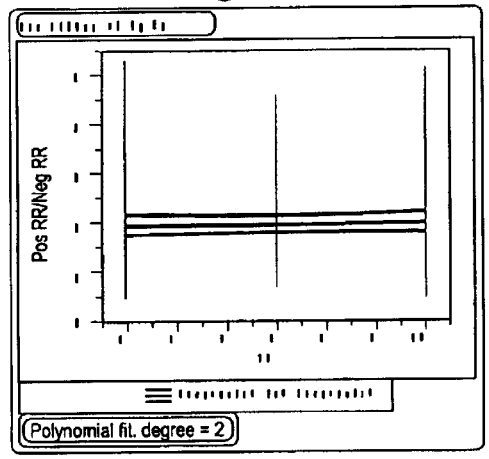
Figure 2D:
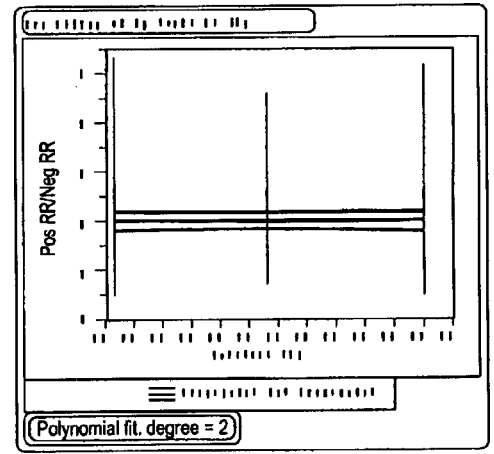
Figure 2E:
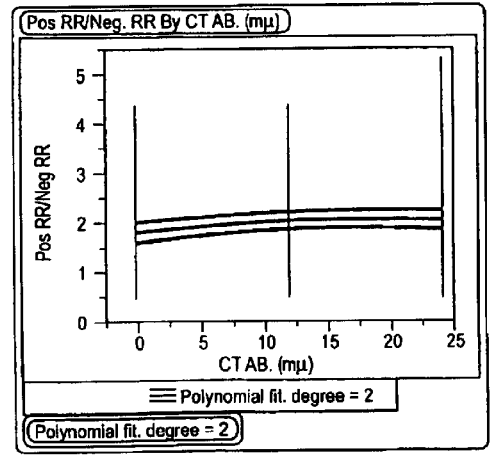
Figure 2F:
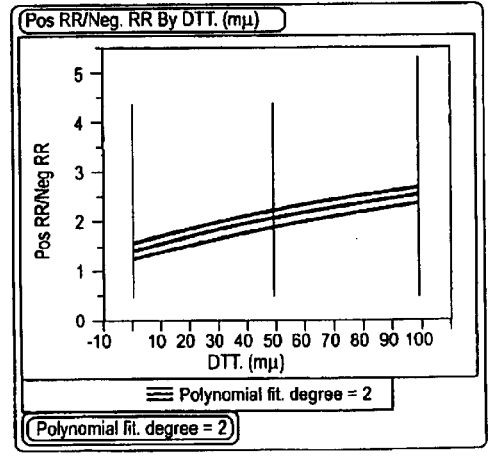

The signals generated from the various samples in the study are represented in Table 5 for the HIV samples and Table 6 for the HBV samples. The tables show the lysis conditions used for the samples and the signals generated for the internal control which was processed with the samples and either the HIV or the HBV signals from the samples. The ratios of the signals from the positive samples to the signals from the negative samples were plotted and analyzed using JMP software from SAS Institute Inc. The results from both the HIV and HBV extractions, FIGS. 1A–1F and FIGS. 2A–2F respectively, show that a wide range of conditions can be used in the process for both HIV and HBV and that many conditions allow for the simultaneous extraction of both HIV and HBV.

TABLE 5

| Pattern | mM CTAB | mM DTT | pH | % Tween-20 | M GITC | Temp | Neg Fam (HIV) | Neg TR (int Ctrl) | Pos Fam (HIV) | Pos TR (int Ctrl) |
|---|---|---|---|---|---|---|---|---|---|---|
| ------ | 0 | 0 | 4 | 13.3 | 3.33 | 35 | 5486.333 | 3692 | 11262 | 8526.333 |
| ----++ | 0 | 0 | 4 | 13.3 | 4.66 | 55 | 4424.667 | 9302 | 11482 | 7854.333 |
| ---+-+ | 0 | 0 | 4 | 24 | 3.33 | 55 | 5666 | 4089.333 | 7072.333 | 5088.333 |
| ---++- | 0 | 0 | 4 | 24 | 4.66 | 35 | 5015.667 | 12252.33 | 19858.67 | 11733 |
| --+--+ | 0 | 0 | 10 | 13.3 | 3.33 | 55 | 4879.333 | 13952 | 21567 | 12767 |
| --+-+- | 0 | 0 | 10 | 13.3 | 4.66 | 35 | 4479.333 | 14033.33 | 23514.67 | 12948 |
| --++-- | 0 | 0 | 10 | 24 | 3.33 | 35 | 4977 | 9272 | 14768 | 7690 |
| --++++ | 0 | 0 | 10 | 24 | 4.66 | 55 | 4806.333 | 10057.33 | 15730.33 | 8273.667 |
| -+---+ | 0 | 100 | 4 | 13.3 | 3.33 | 55 | 5393 | 6056.333 | 9859.333 | 6102.333 |
| -+--+- | 0 | 100 | 4 | 13.3 | 4.66 | 35 | 5483.667 | 11603.67 | 14634.67 | 9215 |
| -+-+-- | 0 | 100 | 4 | 24 | 3.33 | 35 | 5834 | 6525.667 | 8937 | 5768.667 |
| -+-+++ | 0 | 100 | 4 | 24 | 4.66 | 55 | 5011.333 | 8967.333 | 11264 | 8388 |
| -++--- | 0 | 100 | 10 | 13.3 | 3.33 | 35 | 4099 | 8307.333 | 11902.33 | 7301.333 |
| -++-++ | 0 | 100 | 10 | 13.3 | 4.66 | 55 | 4374.667 | 3469.333 | 5251.333 | 3742.667 |
| -+++-+ | 0 | 100 | 10 | 24 | 3.33 | 55 | 4273.667 | 5029 | 7707 | 4766 |
| -++++- | 0 | 100 | 10 | 24 | 4.66 | 35 | 4448.333 | 10494 | 19596.33 | 10200.67 |
| +----+ | 24 | 0 | 4 | 13.3 | 3.33 | 55 | 5432 | 8296 | 14120 | 9926.333 |
| +---+- | 24 | 0 | 4 | 13.3 | 4.66 | 35 | 4669.333 | 13721.67 | 15696 | 12326 |
| +--+-- | 24 | 0 | 4 | 24 | 3.33 | 35 | 5425.667 | 5036 | 12432.67 | 7527 |
| +--+++ | 24 | 0 | 4 | 24 | 4.66 | 55 | 4964.667 | 10306.33 | 14561 | 9487 |
| +-+--- | 24 | 0 | 10 | 13.3 | 3.33 | 35 | 4827.333 | 15834 | 15675.33 | 12000 |
| +-+-++ | 24 | 0 | 10 | 13.3 | 4.66 | 55 | 4698.333 | 9623.667 | 15484.67 | 7829 |
| +-++-+ | 24 | 0 | 10 | 24 | 3.33 | 55 | 4667 | 10944.33 | 12604 | 6841 |
| +-+++- | 24 | 0 | 10 | 24 | 4.66 | 35 | 4761.333 | 11392.33 | 18971.67 | 9964.333 |
| ++---- | 24 | 100 | 4 | 13.3 | 3.33 | 35 | 5615 | 5676.333 | 12048.67 | 8041.667 |
| ++--++ | 24 | 100 | 4 | 13.3 | 4.66 | 55 | 4729.333 | 6406 | 10190.67 | 6842 |
| ++-+-+ | 24 | 100 | 4 | 24 | 3.33 | 55 | 4918 | 4094 | 5869.667 | 4057.333 |
| ++-++- | 24 | 100 | 4 | 24 | 4.66 | 35 | 5823 | 12712.33 | 17049.67 | 9150 |
| +++--+ | 24 | 100 | 10 | 13.3 | 3.33 | 55 | 4287 | 4109 | 6732.333 | 4039 |
| +++-+- | 24 | 100 | 10 | 13.3 | 4.66 | 35 | 4724.667 | 6374 | 11157.33 | 5757 |
| ++++-- | 24 | 100 | 10 | 24 | 3.33 | 35 | 4672.333 | 9511.333 | 15455 | 7734 |
| ++++++ | 24 | 100 | 10 | 24 | 4.66 | 55 | 3979.333 | 3732 | 5256.667 | 3812 |
| 000000 | 12 | 50 | 7 | 18.65 | 3.995 | 45 | 4850.833 | 13233.87 | 21264.6 | 11335.3 |
| -00000 | 0 | 50 | 7 | 18.65 | 3.995 | 45 | 4921 | 14609.67 | 27921.67 | 11625.67 |
| +00000 | 24 | 50 | 7 | 18.65 | 3.995 | 45 | 4405.667 | 14558.33 | 25260 | 11686 |
| 0-0000 | 12 | 0 | 7 | 18.65 | 3.995 | 45 | 4490.333 | 13230.33 | 24602.33 | 11658 |
| 0+0000 | 12 | 100 | 7 | 18.65 | 3.995 | 45 | 4585.667 | 10166 | 19681.33 | 8925.333 |
| 00-000 | 12 | 50 | 4 | 18.65 | 3.995 | 45 | 5469.667 | 9663.333 | 15432.33 | 7177.667 |
| 00+000 | 12 | 50 | 10 | 18.65 | 3.995 | 45 | 4450.667 | 8384.333 | 16545.67 | 5780.667 |
| 000-00 | 12 | 50 | 7 | 13.3 | 3.995 | 45 | 4665 | 10743 | 21749 | 10346.33 |
| 000+00 | 12 | 50 | 7 | 24 | 3.995 | 45 | 4551 | 10010.33 | 21181.33 | 8998667 |
| 0000-0 | 12 | 50 | 7 | 18.65 | 3.33 | 45 | 4614.667 | 10809.67 | 23293.33 | 11219 |
| 0000+0 | 12 | 50 | 7 | 18.65 | 4.66 | 45 | 4811.33 | 13213 | 22731.67 | 10757.33 |
| 00000- | 12 | 50 | 7 | 18.65 | 3.995 | 35 | 5195 | 12653 | 21010.33 | 8770.667 |
| 00000+ | 12 | 50 | 7 | 18.65 | 3.995 | 55 | 4798.667 | 11609 | 20922 | 8777.333 |

TABLE 6

| Pattern | mM CTAB | mM DTT | pH | % Tween-20 | M GITC | Temp | Neg Fam (HBV) | Neg TR (int Ctrl) | Pos Fam (HBV) | Pos TR (int Ctrl) |
|---|---|---|---|---|---|---|---|---|---|---|
| ------ | 0 | 0 | 4 | 13.3 | 3.33 | 35 | 13763 | 15857 | 19806 | 18835 |
| ----++ | 0 | 0 | 4 | 13.3 | 4.66 | 55 | 12691 | 16123 | 24121 | 16359 |
| ---+-+ | 0 | 0 | 4 | 24 | 3.33 | 55 | 16384 | 20296 | 20057 | 18493 |
| ---++- | 0 | 0 | 4 | 24 | 4.66 | 35 | 13143 | 19228 | 17052 | 21522 |
| --+--+ | 0 | 0 | 10 | 13.3 | 3.33 | 55 | 16249 | 20133 | 22242 | 22616 |
| --+-+- | 0 | 0 | 10 | 13.3 | 4.66 | 35 | 13593 | 24713 | 19682 | 26061 |
| --++-- | 0 | 0 | 10 | 24 | 3.33 | 35 | 14912 | 19756 | 19189 | 22207 |
| --++++ | 0 | 0 | 10 | 24 | 4.66 | 55 | 15950 | 27230 | 18497 | 24681 |
| -+---+ | 0 | 100 | 4 | 13.3 | 3.33 | 55 | 15319 | 23021 | 27155 | 19706 |
| -+--+- | 0 | 100 | 4 | 13.3 | 4.66 | 35 | 16135 | 24778 | 26854 | 20820 |
| -+-+-- | 0 | 100 | 4 | 24 | 3.33 | 35 | 17592 | 21386 | 27391 | 20735 |
| -+-+++ | 0 | 100 | 4 | 24 | 4.66 | 55 | 14416 | 22597 | 27652 | 17980 |
| -++--- | 0 | 100 | 10 | 13.3 | 3.33 | 35 | 12321 | 17029 | 27663 | 18062 |
| -++-++ | 0 | 100 | 10 | 13.3 | 4.66 | 55 | 12937 | 24453 | 32857 | 19601 |
| -+++-+ | 0 | 100 | 10 | 24 | 3.33 | 55 | 13406 | 23679 | 28120 | 19813 |
| -++++- | 0 | 100 | 10 | 24 | 4.66 | 35 | 14247 | 23632 | 29093 | 19725 |
| +----+ | 24 | 0 | 4 | 13.3 | 3.33 | 55 | 14825 | 22245 | 27359 | 21866 |
| +---+- | 24 | 0 | 4 | 13.3 | 4.66 | 35 | 14557 | 20537 | 19770 | 19482 |
| +--+-- | 24 | 0 | 4 | 24 | 3.33 | 35 | 16013 | 19770 | 18575 | 14349 |
| +--+++ | 24 | 0 | 4 | 24 | 4.66 | 55 | 14816 | 21794 | 24068 | 18830 |
| +-+--- | 24 | 0 | 10 | 13.3 | 3.33 | 35 | 14828 | 13285 | 16079 | 9985 |
| +-+-++ | 24 | 0 | 10 | 13.3 | 4.66 | 55 | 14470 | 19531 | 16739 | 21070 |
| +-++-+ | 24 | 0 | 10 | 24 | 3.33 | 55 | 15201 | 23681 | 14966 | 18047 |
| +-+++- | 24 | 0 | 10 | 24 | 4.66 | 35 | 15645 | 18663 | 17625 | 21305 |
| ++---- | 24 | 100 | 4 | 13.3 | 3.33 | 35 | 14931 | 21110 | 27690 | 20362 |
| ++--++ | 24 | 100 | 4 | 13.3 | 4.66 | 55 | 13502 | 17549 | 29140 | 16016 |
| ++-+-+ | 24 | 100 | 4 | 24 | 3.33 | 55 | 13904 | 20313 | 24367 | 14119 |
| ++-++- | 24 | 100 | 4 | 24 | 4.66 | 35 | 15840 | 26220 | 29686 | 21216 |
| +++--+ | 24 | 100 | 10 | 13.3 | 3.33 | 55 | 14098 | 20319 | 26624 | 16095 |
| +++-+- | 24 | 100 | 10 | 13.3 | 4.66 | 35 | 15464 | 27136 | 34458 | 17911 |
| ++++-- | 24 | 100 | 10 | 24 | 3.33 | 35 | 15052 | 24848 | 29940 | 20050 |
| ++++++ | 24 | 100 | 10 | 24 | 4.66 | 55 | 13094 | 19608 | 25388 | 14897 |
| 000000 | 12 | 50 | 7 | 18.65 | 3.995 | 45 | 14548 | 23128 | 24077 | 19954 |
| -00000 | 0 | 50 | 7 | 18.65 | 3.995 | 45 | 13771 | 24107 | 18997 | 24754 |
| +00000 | 24 | 50 | 7 | 18.65 | 3.995 | 45 | 12406 | 23835 | 17921 | 21838 |
| 0-0000 | 12 | 0 | 7 | 18.65 | 3.995 | 45 | 12699 | 23712 | 19340 | 24507 |
| 0+0000 | 12 | 100 | 7 | 18.65 | 3.995 | 45 | 13936 | 25988 | 26736 | 19736 |
| 00-000 | 12 | 50 | 4 | 18.65 | 3.995 | 45 | 14715 | 26245 | 27755 | 18442 |
| 00+000 | 12 | 50 | 10 | 18.65 | 3.995 | 45 | 13446 | 25754 | 26293 | 18507 |
| 000-00 | 12 | 50 | 7 | 13.3 | 3.995 | 45 | 12827 | 23411 | 23485 | 18005 |
| 000+00 | 12 | 50 | 7 | 24 | 3.995 | 45 | 13103 | 23340 | 25270 | 20891 |
| 0000-0 | 12 | 50 | 7 | 18.65 | 3.33 | 45 | 13992 | 24536 | 24898 | 21251 |
| 0000+0 | 12 | 50 | 7 | 18.65 | 4.66 | 45 | 14545 | 25227 | 25865 | 21429 |
| 00000- | 12 | 50 | 7 | 18.65 | 3.995 | 35 | 15186 | 25297 | 23463 | 19417 |
| 00000+ | 12 | 50 | 7 | 18.65 | 3.995 | 55 | 15190 | 27421 | 23149 | 20780 |

Example 6

Extraction of Nucleic Acids from *Chlamydia Trachomatis* and *Neiseria Gonorrhoeae* in Urine In this example, nucleic acids were extracted from one ml of urine that contained both *Chlamydia trachomatis* and *Neiseria gonorrhoeae* using the metal oxide method described above. Nucleic acids from the urine samples were also extracted using the LCx® Urine Specimen Preparation Kit. The extracted samples were tested for both *Chlamydia trachomatis* and *Neiseria gonorrhoeae* using LCx® assays from Abbott Laboratories.

The sample panels were made up using pooled urine that was tested to be negative for both *Chlamydia trachomatis* and *Neiseria gonorrhoeae* using (assays from Abbott Laboratories. Positive urine panels were made by adding positive stocks of *C. trachomatis* and *N. gonorrhoeae* to the negative urine. The "low positive" panel contained 0.5 elementary bodies (EB) of *C. trachomatis* and 0.5 colony forming units (cfu) of *N. gonorrhoeae* per ml of urine. The "high positive" panel contained 10 EB of *C. trachomatis* and 10 cfu of *N. gonorrhoeae* per ml of urine.

The respective sample preparation procedures were performed on 1 ml of urine samples from each of the two test panels and the negative control. The metal oxide procedure was performed by mixing 1 ml of test urine sample with 3 ml of lysis buffer (4.3M guanidinium isothiocyanate, 18% Tween-20, 12 mM cetyltrimethylammonium bromide, 50 mM dithiothreitol, 100 mM Tris, pH 7.6) and 5 mg of $Fe_2O_3$ particles (M-2038, ISK Corporation). The extraction mix also contained 7.5 micrograms of polyA RNA as carrier. The lysate was incubated at 45° C. for 20 minutes. The particles were captured magnetically and the lysate removed by aspiration. The particles were washed twice with a 2 M GITC, 5% tween-20, 50 mM K acetate pH 6.0, and twice with 50 mM Tris buffer, pH 8.0, 0.45% Na azide. After the wash solution was aspirated, 100 microliters of elution buffer was added to the tubes containing the washed particles. The elution buffer was water with 0.045% Na azide as a preservative. After addition of the elution buffer, the particles were resuspended by pipetting and the suspension was incubated at 70° C. for 20 minutes. After incubation the particles were captured on the sides of the tubes using a magnetic rack and the eluant removed. The 100 microliters recovered from the sample was then diluted with 900 microliters of LCx® Urine Specimen Resuspension Buffer (50 mM MgCl2 and detergent). The resuspension buffer must be added to the extracted samples to add the MgCl2 needed in the assay. 50 microliters of the sample was then used in the *Chlamydia trachomatis* and *Neiseria gonorrhoeae* LCx® assays from Abbott Laboratories.

The samples were also prepared using the LCx® Urine Sample Preparation Kit. 1 ml urine samples were centrifuged at 9,000×g for 15 minutes and the suupematant was removed. 900 microliters of LCx® Urine Specimen Resuspension Buffer was added to the pellet and the sample vortexed to resuspend the sample. The sample was then heated at 97° C. for 15 minutes to release the DNA. After cooling, 100 microliters of the elution buffer (water and 0.045% Na azide) used for the metal oxide process was added to the extracted samples to equilibrate the concentration of components to the metal oxide extracted samples. 50 microliters of the sample was then used in the *Chlamydia trachomatis* and *Neiseria gonorrhoeae*® assays from Abbott Laboratories. Negative and positive controls were also run in the assays. The results for the *Chlamydia trachomatis* assays included a negative control which had a 0 rate signal and a positive control which had a rate signal of 1600. The remaining results for the *Chlamydia trachomatis* assays are shown in Table 7. The results for the *Neiseria gonorrhoeae* assays included a positive control which had a rate signal of 0 and a positive control which had a rate signal of 950. The remaining results for the *Neiseria gonorrhoeae* assays are shown in Table 8. The metal oxide process performed as well as the standard extraction method for the LCx® assays for both cell types.

TABLE 7

| Assay Type & Sample Concentration | Rate |
| --- | --- |
| LCx ® Negative Urine | 0 |
| LCx ® Low Positive Urine | 1000 |
| LCx ® High Positive Urine | 1900 |
| $Fe_2O_3$ Negative Urine | 0 |
| $Fe_2O_3$ Low Positive Urine | 1400 |
| $Fe_2O_3$ High Positive Urine | 1900 |

TABLE 8

| Assay Type & Sample Concentration | Rate |
| --- | --- |
| LCx ® Negative Urine | 0 |
| LCx ® Low Positive Urine | 450 |
| LCx ® High Positive Urine | 1000 |
| $Fe_2O_3$ Negative Urine | 0 |
| $Fe_2O_3$ Low Positive Urine | 500 |
| $Fe_2O_3$ High Positive Urine | 1000 |

What is claimed is:

1. A method for separating nucleic acid from a test sample comprising:
   a) contacting a test sample with a metal oxide support material and a binding buffer such that the nucleic acid bonds with the metal oxide support material to form complexes without prior purification or precipitation of the nucleic acid, wherein the binding buffer comprises a chaotropic agent and
      a detergent
   and wherein the binding buffer contains no or a low concentration of organic solvent such that the flashpoint of the binding buffer is greater than 130 degrees Fahrenheit;
   b) separating the complexes from the test sample; and
   c) eluting the nucleic acid from the metal oxide support material, thereby separating the nucleic acid from the test sample,
   wherein step a) allows the nucleic acids to be directly employed in an amplification reaction without exchanging an elution buffer and wherein the test sample is selected from the group consisting of blood, ocular lens fluid, cerebral fluid, milk, ascites fluid, synovial fluid, peritoneal fluid, amniotic fluid, tissue, fermentation broth, and cell culture.

2. The method of claim 1 wherein the binding buffer further comprises a reducing agent.

3. The method of claim 1 further comprising a wash step after separating the complexes from the test sample and before eluting the nucleic acid from the metal oxide support material.

4. The method of claim 1 wherein eluting the nucleic acid from the metal oxide support material comprises contacting the complexes with a reagent selected from the group consisting of water and a phosphate containing buffer.

5. The method of claim 4 further comprising the step of detecting the nucleic acid after the eluting the nucleic acid from the metal oxide support material.

6. The method of claim 5 further comprising the step of amplifying the nucleic acid after eluting the nucleic acid from the metal oxide support material and before detecting the nucleic acid.

7. The method of claim 5 wherein the nucleic acid is separated from a test sample comprising more than one source of nucleic acid.

8. The method of claim 7 wherein the nucleic acid separated from the test sample comprises RNA and DNA.

9. The method of claim 6 wherein the step of amplifying the nucleic acid is performed without removal of the elution buffer.

10. The method of claim 1 wherein eluting the nucleic acid from the metal oxide support material comprises contacting the complexes with an elution buffer having a pH of between 6 and 10.

11. The method of claim 1 wherein eluting the nucleic acid from the metal oxide support material comprises contacting the complexes with an elution buffer having a pH of between 7 and 9.

12. The method of claim 1 wherein eluting the nucleic acid from the metal oxide support material comprises contacting the complexes with an elution buffer comprising a sodium phosphate or organophosphate compound such that the phosphate concentration in the elution buffer is from 10 mM to 300 mM.

13. The method of claim 1 wherein eluting the nucleic acid from the metal oxide support material comprises contacting the complexes with an elution buffer comprising a sodium phosphate or organophosphate compound such that the phosphate concentration in the elution buffer is from 10 mM to 100 mM.

14. The method of claim 1 wherein the nucleic acid is HIV nucleic acid from plasma.

15. The method of claim 1 wherein the nucleic acid is HBV nucleic acid from plasma.

* * * * *

SEQUENCE LISTING

```
<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: HIV forward primer

<400> SEQUENCE: 1
attccctaca atccccaaag tcaaggagt                                       29

<210> SEQ ID NO 2
<211> LENGTH: 22
<212> TYPE: DNA
<213> ORGANISM: Artificial Sequence
<220> FEATURE:
<223> OTHER INFORMATION: HIV reverse primer

<400> SEQUENCE: 2
cctgcactgt accccccaat cc                                              22

<210> SEQ ID NO 3
<211> LENGTH: 28
<212> TYPE: DNA
<213> ORGANISM: Artificial Sequence
<220> FEATURE:
<223> OTHER INFORMATION: HIV beacon probe

<400> SEQUENCE: 3
gcgagacagc agtacaaatg gcactcgc                                        28

<210> SEQ ID NO 4
<211> LENGTH: 23
```

```
-continued

<212> TYPE: DNA
<213> ORGANISM: Artificial Sequence
<220> FEATURE:
<223> OTHER INFORMATION: HBV forward primer

<400> SEQUENCE: 4
tctttcggag tgtggattcg cac                                              23

<210> SEQ ID NO 5
<211> LENGTH: 27
<212> TYPE: DNA
<213> ORGANISM: Artificial Sequence
<220> FEATURE:
<223> OTHER INFORMATION: HBV reverse primer

<400> SEQUENCE: 5
ctaacattga gattcccgag attgaga                                          27

<210> SEQ ID NO 6
<211> LENGTH: 34
<212> TYPE: DNA
<213> ORGANISM: Artificial Sequence
<220> FEATURE:
<223> OTHER INFORMATION: HBV beacon probe

<400> SEQUENCE: 6
ctcgctcccc tagaagaaga actccctcgg cgag                                  34
```